(12) United States Patent
Hernández et al.

(10) Patent No.: US 8,263,385 B2
(45) Date of Patent: Sep. 11, 2012

(54) S-TRIAZINE-HERBICIDE-DEGRADING BACTERIA, PRODUCT FOR THE BIOREMEDIATION AND METHOD OF BIOREMEDIATION

(75) Inventors: Marcela Hernández, Valparaiso (CL);
Verónica Morgante, Valparaiso (CL);
Patricio Villalobos, Valparaiso (CL);
Cecilia Flores, Valparaiso (CL);
Myriam González, Valparaiso (CL);
Michael Seeger, Valparaiso (CL)

(73) Assignee: Universidad Technica Fedrico Santa Maria, Valparaiso (CL)

( * ) Notice: Subject to any disclaimer, the term of this patent is extended or adjusted under 35 U.S.C. 154(b) by 1105 days.

(21) Appl. No.: 12/166,961

(22) Filed: Jul. 2, 2008

(65) Prior Publication Data
US 2009/0017525 A1   Jan. 15, 2009

(30) Foreign Application Priority Data

Jul. 6, 2007  (CL) .................................. 1982-2007

(51) Int. Cl.
*A01N 63/00* (2006.01)
*B09C 1/10* (2006.01)
*C02F 3/00* (2006.01)
*C02F 3/34* (2006.01)
*C12N 1/20* (2006.01)

(52) U.S. Cl. .................. 435/262.5; 210/601; 424/93.47; 435/253.3; 435/262; 435/874

(58) Field of Classification Search .......... None
See application file for complete search history.

(56) References Cited

U.S. PATENT DOCUMENTS

| | | | | |
|---|---|---|---|---|
| 5,397,755 | A | * | 3/1995 | Parker et al. ........................ 502/7 |
| 5,508,193 | A | | 4/1996 | Mandelbaum et al. |
| 5,518,910 | A | * | 5/1996 | Parker et al. .................... 435/176 |
| 5,980,747 | A | * | 11/1999 | Vandenbergh et al. ........ 210/611 |
| 6,762,047 | B2 | * | 7/2004 | Vandenbergh ............. 435/252.34 |
| 2006/0128946 | A1 | * | 6/2006 | Weiner et al. .................. 530/370 |

FOREIGN PATENT DOCUMENTS

| | | |
|---|---|---|
| CA | 2636856 | 11/2011 |
| WO | 03025627 | * 3/2003 |

OTHER PUBLICATIONS

Cheng et al. "Allophanate Hydrolase, Not Urease, Functions in Bacterial Cyanuric Acid Metabolism." *Applied & Environmental Microbiology.* vol. 71. No. 8. 2005. pp. 4437-4445.
De Souza et al. "The Atrazine Catabolism Genes atzABC Are Widesread and Highly Conserved." *Journal of Bacteriology.* vol. 180. No. 7. 1998. pp. 1951-1954.
Cassidy et al. "Environmental applications of immobilized microbial cells: a review." *Journal of Industrial Microbiology.* vol. 16. 1996. pp. 79-101.
Tappe et al. "Diffuse atrazine pollution in German aquifers." *Biodegradation.* vol. 13. 2002. pp. 3-10.
Rousseaux et al. "Isolation and characterization of new Gram-negative and Gram-positive atrazine degrading bacteria from different French soils." *FEMS Microbiology Ecology.* vol. 36. 2001. pp. 211-222.
Morán, A. C., Muller, A., Manzano, M., González, B. 2006. Simazine treatment history determines a significant herbicide degradation potential in soils that is not improved by bioaugmentation with *Pseudomonas* sp. ADP. J. Appl. Microbiol. 101: 26-35.
Garcia-González, V., Govantes, F., Shaw, L. J., Burns, R. G., y Santero, E. 2003. Nitrogen control of atrazine utilization in *Pseudomonas* sp. strain ADP. Appl. Environ. Microbiol. 69: 6987-6993.
Hernández, M, Villalobos, P., Morgante, V., González, M., Reiff, C., Moore E. and Seeger, M. 2008. Isolation and characterization of a novel simazine-degrading bacterium from Chilean agricultural soils, *Pseudomonas* sp. MHP41. FEMs Microbiol. Lett. 286: 184-190.

* cited by examiner

*Primary Examiner* — Debbie K Ware
(74) *Attorney, Agent, or Firm* — Merchant & Gould P.C.

(57) ABSTRACT

The present invention provides a bacterial strain which is able to degrade or mineralize s-triazine compounds, such as simazine, which corresponds to *Pseudomonas* sp. strain MHP41, deposited under the accession number NRRL B-30908. The present invention provides a product for the bioremediation of environments contaminated with s-triazine, where the product includes a bacterial inoculum of *Pseudomonas* sp. strain MHP41. The present invention further provides a method for the bioremediation of environments contaminated with s-triazines, which uses this product for the bioremediation.

12 Claims, 9 Drawing Sheets

S-TRIAZINE-HERBICIDE-DEGRADING BACTERIA, PRODUCT FOR THE BIOREMEDIATION AND METHOD OF BIOREMEDIATION

The present invention relates to a bacterial strain that has the ability to degrade s-triazine herbicides, a product that contains this microorganism and an application method of said product for bioremediation of s-triazine-contaminated environments.

BACKGROUND OF THE INVENTION s-Triazines are a family of herbicides that has a symmetric heterocyclic aromatic ring with 6 alternating carbon and nitrogen atoms. Simazine and atrazine are the most relevant members of the s-triazine herbicide family among other less-used compounds such as hydroxysimazine, deethylhydroxysimazine, hydroxyatrazine, deethylatrazine, deethylhydroxyatrazine, deisopropylatrazine, fluoroatrazine, propazine, terbutylazine, cyanuric acid and cyanazine. Both simazine (IUPAC: 6-chloro-$N^2,N^4$-diethyl-1,3,5-triazine-2,4-diamine) and atrazine (IUPAC: 6-chloro-$N^2$-ethyl-$N^4$-isopropyl-1,3,5-triazine-2,4-diamine) are s-triazine herbicides that have a chlorine atom bound to the heterocyclic ring. The mechanism of this herbicide family comprises the inhibition of electron transport in the photosynthesis process.

s-Triazines, especially simazine and atrazine, have been widely used for the control of weeds in many agricultural regions of the world. In Chile, simazine is commonly used for agricultural and forestry practices.

In spite of their advantageous use as herbicides, s-triazines are environmental contaminants that can affect human health and ecosystems. It has been shown that atrazine and other s-triazines can induce breast cancer in rats. Therefore they have been classified as "possible human carcinogen" class-C by EPA (Tappe et al., 2002). Various ecosystems have been chemically perturbed by the constant use of s-triazine herbicides, especially simazine and atrazine. Due to their high mobility, these compounds can cause serious soil and ground water contamination. Therefore these herbicides frequently exceed the standard advisory levels of 0.1 μg $L^{-1}$ and 3.0 μg $L^{-1}$ by the European Union and USA regulatory authorities, respectively (Rousseaux et al., 2001).

Despite this background, the global manufacture and sales of herbicides have raised and showed an increase trend from the 1980 decade. Statistics of the United Nations Food and Agriculture Organization carried out from the early XXI century reveal that herbicide consumption, and especially s-triazines, is high both in the European Union and in the US. According to these statistics, US, France and Germany are the main countries that export s-triazine herbicides.

According to the Environmental Protection Agency (EPA), the global market for pesticides during years 2000 and 2001 was more than 2.3 million tons. Only in the US 0.7 million tons were consumed during years 2000 and 2001, which represents about 40% of the herbicide world market and more than 30% of the pesticide world market. In the US, atrazine is the most employed herbicide for weed control in corn, citric, vine and fruit tree plantations, whereas simazine is mainly used in corn crops.

Due to the extensive use of s-triazines for weed control, simazine and atrazine presence has been detected in surface and ground water in several countries such as the US, Switzerland, South Africa and Germany. In Chile, according to the Servicio Agrícola Ganadero de Chile SAG) (Declaración de ventas de plaguicidas de uso agrícola, Ministerio de Agricultura de Chile, 2006), the pesticide consumption during 2004 was about 23,000 tons. Important agricultural plantations (avocado, citruses and grape) in Chile are treated with pre-emergent herbicides such as atrazine or simazine. The use of these herbicides reached 350 tons, representing about 10% of the herbicide used in the country. In the last time, the massive use of agrochemicals has motivated the study of environments that are potentially affected by these compounds. Recent studies have detected s-triazine compounds in agricultural watershed at south-central Chile.

Therefore environmental contamination by s-triazines is a worldwide problem, which requires urgent attention.

One interesting alternative to mitigate s-triazines contamination is bioremediation, which employs microorganisms able to degrade these pollutants or transform them into innocuous compounds for the environment and human health. Some s-triazine-degrading consortia or pure bacterial strains have been isolated, such as *Pseudaminobacter, Nocardioides* sp. and *Agrobacterium. Pseudomonas* sp. ADP strain (Mandelbaum and Wacket, 1996) is able to mineralize s-triazines due to specific catabolic pathways well described in the state of the art. Probably, this is the best-known and one of the most characterized strains of the atrazine-degrading microorganisms.

Nevertheless, efficient microorganisms able to degrade s-triazines in the environment are still required.

This technical problem has been solved in the present invention, by the selection of a native bacterium able to degrade s-triazines, i.e. *Pseudomonas* sp. strain MHP41. In addition, the present invention describes a product that contains strain MHP41 and a method for the bioremediation of s-triazine-polluted environments that uses said product.

SUMMARY OF THE INVENTION

The present invention relates to a bacterial strain, which is capable to degrade s-triazine herbicides.

In one aspect of the present invention, these s-triazine compounds are selected from the group consisting of chlorinated compounds, wherein simazine and atrazine were selected from the chlorinated s-triazines.

In a preferred embodiment of the present invention, the bacterial strain *Pseudomonas* sp. strain MHP41 which has been deposited in a microorganism collection called Agricultural Research Culture Collection (NRRL) from Peoria, Ill., United States, under the access number B-30908, on Mar. 17, 2006, which is able to grow and completely degrade simazine.

Furthermore, the present invention discloses a product containing this microorganism.

The present invention also comprises a method for the treatment or bioremediation of an environment contaminated with s-triazine-compounds wherein this method comprises the stages of: i) adding *Pseudomonas* sp. strain MHP41 (NRRL B-30908) to said s-triazine-polluted environment, where this bacterium is able to degrade s-triazine compounds, and ii) incubating this bacterium, *Pseudomonas* sp. strain MHP41 (NRRL B-30908), in the contaminated environment during a period of time sufficient to permit the complete degradation the s-triazine compounds present in the environment and the bioremediation thereof.

The present invention also discloses *Pseudomonas* sp. strain MHP41 (NRRL B-30908), a native bacterial strain isolated from soil. This bacterium belong to the genus *Pseudomonas*, is easily cultivated, reaches high cellular densities and shows fast grow under laboratory conditions. This strain grows at 30° C. from a turbidity measured at 600 nm of 0.082 (1×10⁵ CFU/ml) to a turbidity at 600 nm of 1.012 (2×10⁸ CFU/ml), in minimal medium using simazine as the single nitrogen source.

DETAILED DESCRIPTION OF THE PREFERRED EMBODIMENT(S)

Figure 1:
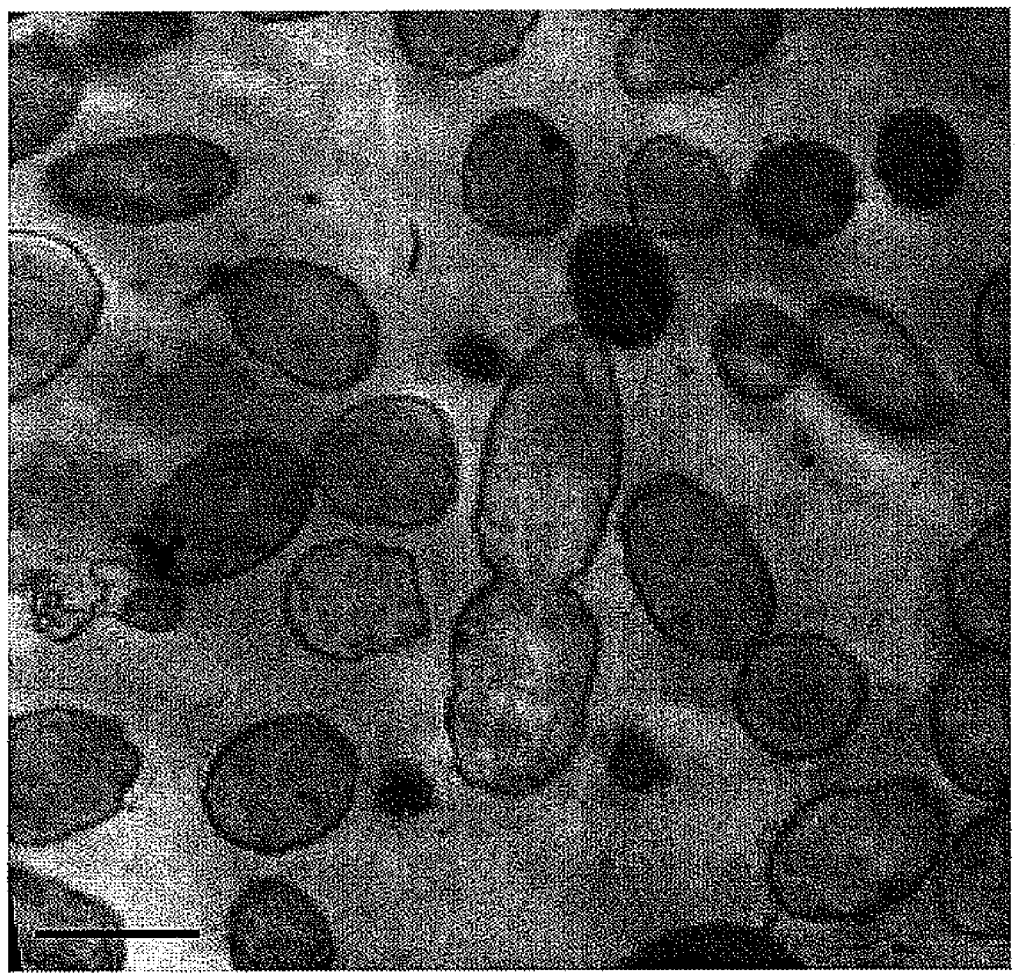
FIG. 1 shows a micrograph of *Pseudomonas* sp. strain MPH41. The micrograph was obtained by transmission electronic microscopy. The bar represents 1 μm.

The present invention is related to a bacterial strain which is able to degrade s-triazine compounds, a product that contains this strain and a bioremediation method for environments polluted with s-triazine compounds.

DEFINITIONS

As used in the present invention the term "s-triazines" refers to molecules having a basic structure that comprises a symmetric heterocyclic aromatic ring with 6 alternating carbon and nitrogen atoms.

As used in the present invention the term "simazine" refers to a s-triazine molecule having carbon atoms substituted with one chlorine atom and two ethylamine groups (IUPAC: 6-chloro-$N^2$,$N^4$-diethyl-1,3,5-triazine-2,4-diamine).

As used in the present invention the term "atrazine" refers to a s-triazine molecule having carbon atoms substituted with one chlorine atom, an ethylamine group and an isopropylamine group (IUPAC: 6-chloro-$N^2$-ethyl-$N^4$-isopropyl-1,3,5-triazine-2,4-diamine).

As used in the present invention the term "degrade" represents the decomposition of a chemical compound, such as s-triazine compound, by a metabolic pathway, to obtain a molecule with lower complexity.

As used in the present invention the term "mineralize" means biological decomposition of an organic compound, such as s-triazine compound, into molecules of minimal complexity.

As used in the present invention the term "bioremediation" means a treatment method to treat an environment or material considered as contaminated waste material located in a defined environment, where said treatment allows transforming this waste material into a less toxic material for the surrounding environment, or transforming this waste material into a material which can be metabolized by a microorganism or group of microorganisms, where this treatment method comprises the application of a living microorganism as a component of the treatment method.

As used in the present invention the term "native bacterium" means a natural bacterium isolated from soil and that were not modified genetically.

As used in the present invention, the term "inoculum" means a concentrated bacterial suspension (free or encapsulated cells) of a known concentration (CFU/ml).

As used in the present invention the term "ribotype" means an identity classification and species and subspecies differentiation based on the RFLP (Restriction Fragment Length Polymorphism) analysis of the 16S rRNA gene.

As used in the present invention the term "buffer solution" means a solution which is able to keep the pH value when acid or base are added.

As used in the present invention the term "lyophilized" refers to a *Pseudomonas* sp. strain MHP41 inoculum subjected to a lyophilization process, which is a method that consists of a fast dehydration under vacuum and at low temperatures, to achieve better product conservation.

As used in the present invention the term "microcosms" refers to a certain volume of soil in a container, whose important variables such as moisture, temperature and presence or absence of microorganisms and/or organic contaminants are known and controlled.

To obtain a bacterial strain able to degrade s-triazine compounds, microorganisms were isolated from agricultural soil samples and selected in a culture medium with simazine as the only nitrogen source. Bacteria were isolated in minimal agar plates with simazine as the only nitrogen source, and individual colonies were isolated from the plates.

A native strain was isolated which is able to degrade s-triazine compounds and to use simazine as the only nitrogen source. This strain was designated as MHP41. The bacterium was identified as a *Pseudomonas* sp., based on a sequence analysis of the 16S rRNA gene and named as *Pseudomonas* sp. strain MHP41.

As was previously discussed in the background of the invention, diverse microorganisms that are able to degrade s-triazines are known in the state of the art, such as *Pseudomonas* sp. ADP. In this microorganism, the s-triazine degradation pathway has been widely studied and characterized, and their catabolic genes are well known. It is probable that another strain able to degrade s-triazines uses the same metabolic pathway and genes. Diagram 1 represents the aerobic process of s-triazine degradation.

*Pseudomonas* sp. strain MHP41 possesses the atzA, atzB, atzC, atzD, atzE and atzF genes. Therefore, the s-triazine degradation pathways of strain MHP41 are similar to the pathways that have been described in the state of the art.

Diagram 1.

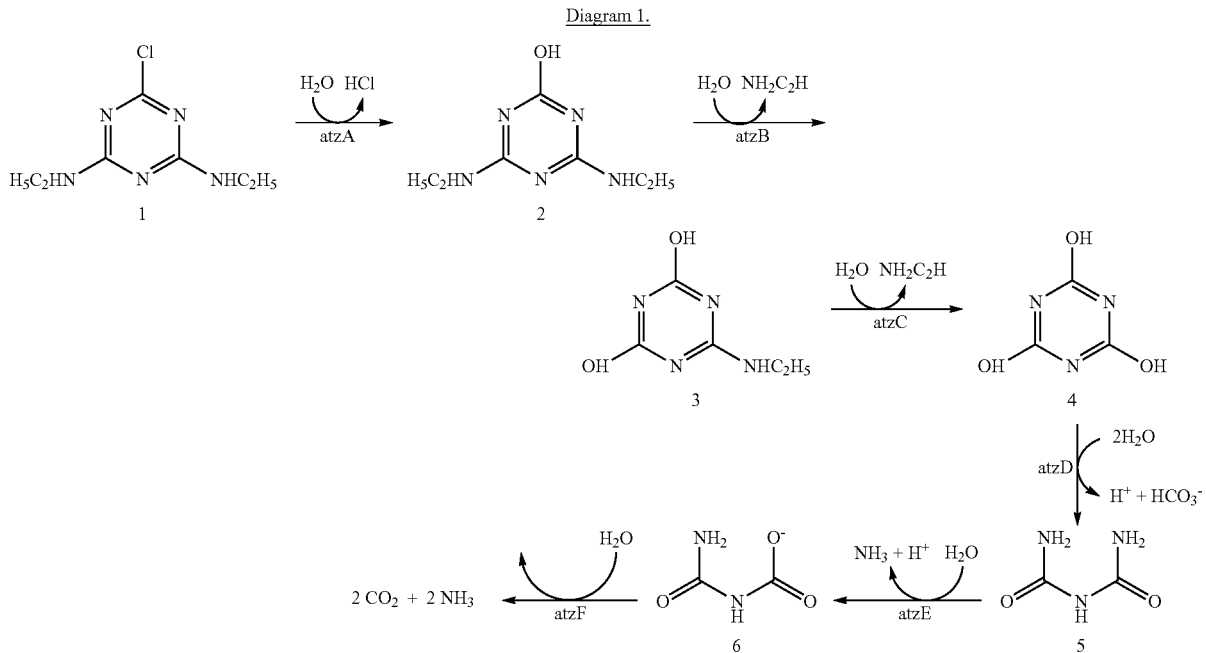

The "upper" degradation pathway for simazine (and other s-triazine herbicides, such as atrazine) is encoded by the atzA, atzB and atzC genes. The first enzyme atrazine chlorohydrolase (AtzA), encoded by atzA gene, catalyses the hydrolytic dechlorination of simazine (1) to yield hydroxysimazine (2), the first metabolite of the catabolic pathway. Subsequent reactions catalyzed by the enzymes hydroxyatrazine ethylaminohydrolase (AtzB)—encoded by atzB gene—and N-isopropylamelide-isopropylaminohydrolase (AtzC)—encoded by atzC gene—transforms the hydroxysimazine (2) to N-ethylamelide (3) and finally to cyanuric acid (4). This step is the last reaction of the upper degradation pathway (de Souza et al., 1998). The "lower" s-triazine degradation pathway involves the enzymes cyanuric acid amidohydrolase (AtzD), biuret hydrolase (AtzE) and allophanate hydrolase (AtzF), which are encoded by the atzD, atzE and atzF genes, respectively. These enzymes transform the compound cyanuric acid to biuret (5) and allophanate (6) and finally into carbon dioxide and ammonia (de Souza et al., 1998; Cheng et al., 2005).

Description of *Pseudomonas* sp. Strain MHP41.

The new *Pseudomonas* sp. strain MHP41 is a Gram-negative, motile, rod-shaped bacterium. It was catalase positive and oxidase negative. The strain MHP41 is able to grow on plates with simazine or atrazine as nitrogen source, showing clearing zones around the colonies that indicate simazine degradation.

The present strain was identified by using the Biolog identification test and the analysis of the 16S rRNA gene sequence. MHP41 was identified as a strain belonging to the genus *Pseudomonas*.

This strain is sensitive to the antibiotics rifampicin, kanamycin, carbamicillin, tetracycline, and streptomycin, and has natural resistance to ampicillin.

The metabolic profile of *Pseudomonas* sp. strain MHP41 is presented in Table 1.

TABLE 1

Carbon sources for metabolism (respiration) of *Pseudomonas* sp. strain MHP41. Studies based on the Biolog microplates identification system.

| Carbon sources on which *Pseudomonas* sp. MHP41 metabolize | Dextrin Glycogen Tween 40 Tween 80 N-acetyl-D-glucosamine α-D-Glucose Acetic Acid Cis-Aconitic Acid | Propionic Acid Shikimic Acid Sebacic Acid Succinic Acid Methyl Pyruvate Bromosuccinic Acid L-Alaninamide | L-Proline D-Serine L-Serine L-Threonine D,L-Carnitine γ-Aminobutyric Acid Urocanic Acid Phenylethylamine |
|---|---|---|---|

TABLE 1-continued

Carbon sources for metabolism (respiration) of
Pseudomonas sp. strain MHP41. Studies based on the Biolog
microplates identification system.

| | | | |
|---|---|---|---|
| | Citric Acid | D-Alanine | Putrescine |
| | Formic Acid | L-Alanine | 2-Aminoethanol |
| | D-Gluconic Acid | L-Alanilglycine | Monomethyl Succinate |
| | α-Hydroxybutyric acid | L-Asparagine | L-Leucine |
| | β-Hydroxybutyric Acid | L-Aspartic Acid | L-Ornithine |
| | Itaconic Acid | L-Glutamic Acid | α-Ketoglutaric Acid |
| | α-Ketobutyric Acid | Glycyl-L-glutamic Acid | α-Ketovaleric Acid |
| | D,L-Lactic Acid | Hydroxy-L-Proline | |
| Carbon | α-Cyclodextrin | D-Melibiose | D-Saccharic Acid |
| sources on | N-Acetyl-D- | β-Methyl D-Glucoside | Succinamic Acid |
| which | galactosamine | | |
| Pseudomonas | Adonitol | D-Psicose | Glucuronamide |
| sp. MHP41 | L-Arabinose | D-Raffinose | Glycyl-L-aspartic Acid |
| does not | | | |
| metabolize | D-Arabitol | L-Rhamnose | L-Histidine |
| | D-Cellobiose | D-Sorbitol | L-Phenylalanine |
| | i-Erithritol | Sucrose | L-Pyroglutamic Acid |
| | L-Fructose | D-Trehalose | Inosine |
| | L-Fucose | Turanose | Uridine |
| | D-Galactose | Xylitol | Thymidine |
| | Gentiobiose | Malonic Acid | 2,3-Butanediol |
| | m-Inositol | D-Galactonic Acid Lactone | Glycerol |
| | α-D-Lactose | D-Galacturonic Acid | D,L-α-Glycerol Phosphate |
| | Lactulose | D-Glucosaminic Acid | Glucose-1-phosphate |
| | Maltose | D-Glucuronic Acid | Glucose-6-phosphate |
| | D-Mannitol | γ-Hydroxybutyric Acid | D-Mannose |
| | p-Hydroxyphenylacetic Acid | | |

Pseudomonas sp. strain MHP41 possesses the atzA, atzB, atzC, atzD, atzE and atzF genes for s-triazine degradation which confer the capability to degrade diverse s-triazine compounds (Table 2). The AtzA enzyme catalyzes the hydrolytic removal of chlorinated and fluorinated substituents from s-triazine molecules, but is unable to remove cyano, azide, methoxy, thiomethyl or amino groups from compounds that are structurally similar to simazine or atrazine.

TABLE 2

Table 2. Chemical structures of s-triazine compounds degraded by the native strain Pseudomonas sp. MHP41.

| Substituents | | | | Degradation |
|---|---|---|---|---|
| R1 | R2 | R3 | s-triazines | |
| Cl | $NHCH_2CH_3$ | $NHCH_2CH_3$ | Simazine | + |
| OH | $NHCH_2CH_3$ | $NHCH_2CH_3$ | Hydroxysimazine | + |
| OH | $NH_2$ | $NHCH_2CH_3$ | Deethylhydroxysimazine | + |
| Cl | $NHCH_2CH_3$ | $NHCH(CH_3)_2$ | Atrazine | + |
| OH | $NHCH_2CH_3$ | $NHCH(CH_3)_2$ | Hydroxyatrazine | + |
| Cl | $NH_2$ | $NHCH(CH_3)_2$ | Deethylatrazine | + |
| OH | $NH_2$ | $NHCH(CH_3)_2$ | Deethylhydroxyatrazine | + |
| Cl | $NHCH_2CH_3$ | $NH_2$ | Deisopropylatrazine | + |
| Cl | $NHCH(CH_3)_2$ | $NHCH(CH_3)_2$ | Propazine | + |
| Cl | $NHCH_2CH_3$ | $NHC(CH_3)_3$ | Terbutylazine | + |
| OH | OH | OH | Cyanuric acid | + |
| Cl | $NHCH_2CH_3$ | $NHC(CH_3)_2CN$ | Cyanazine | + |
| F | $NHCH_2CH_3$ | $NHCH(CH_3)_2$ | Fluoroatrazine | + |

FIG. 1 shows a micrograph of Pseudomonas sp. strain MPH41, the bacterium of the present invention. The micrograph was obtained by transmission electronic microscopy.

Figure 2:
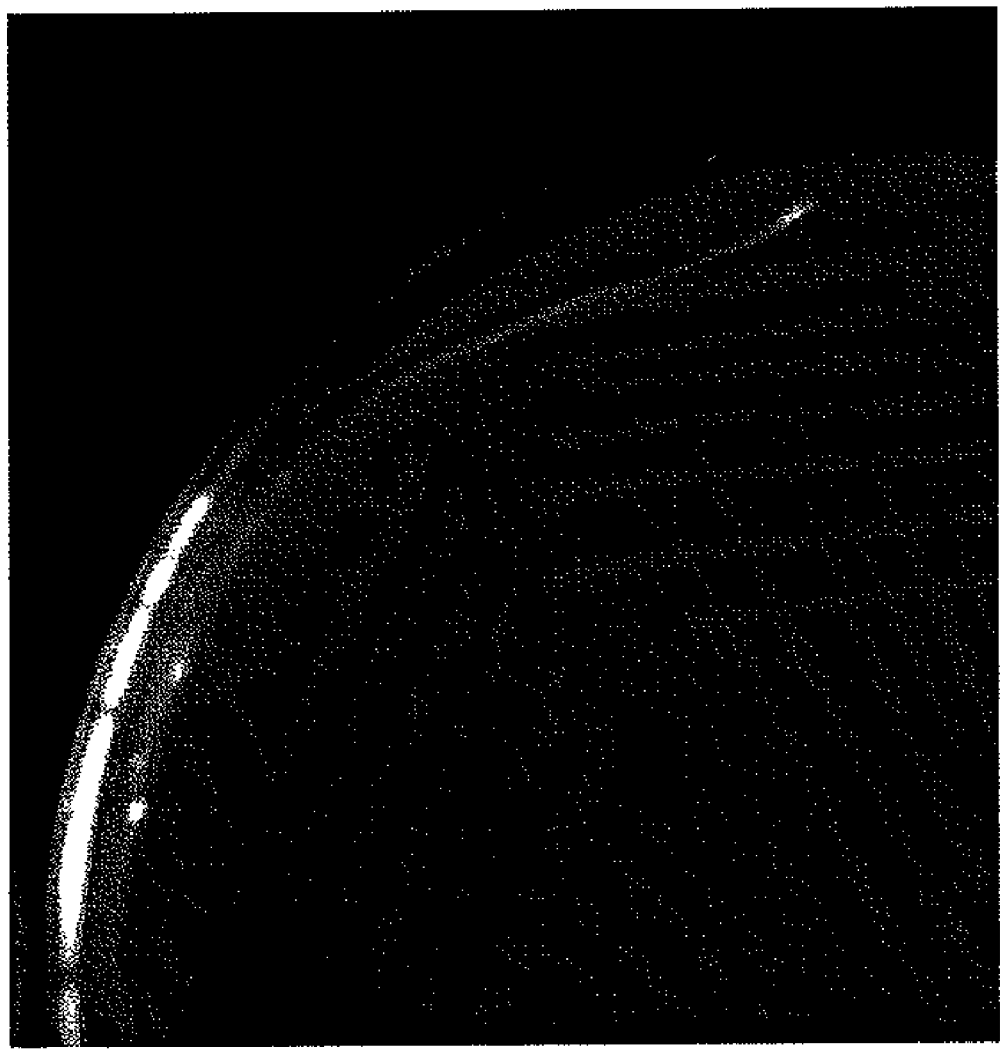
FIG. 2 shows a photograph of a colonies of *Pseudomonas* sp. strain MPH41 growing on minimal medium agar plates with simazine as the sole nitrogen source. Simazine degradation is visualized by clearing zones around the colonies.

FIG. 2 shows a colony photograph of Pseudomonas sp. strain MPH41 growing on minimal medium agar plate with simazine as the sole nitrogen source. Simazine degradation is visualized by clearing zones around the colonies.

Figure 3:
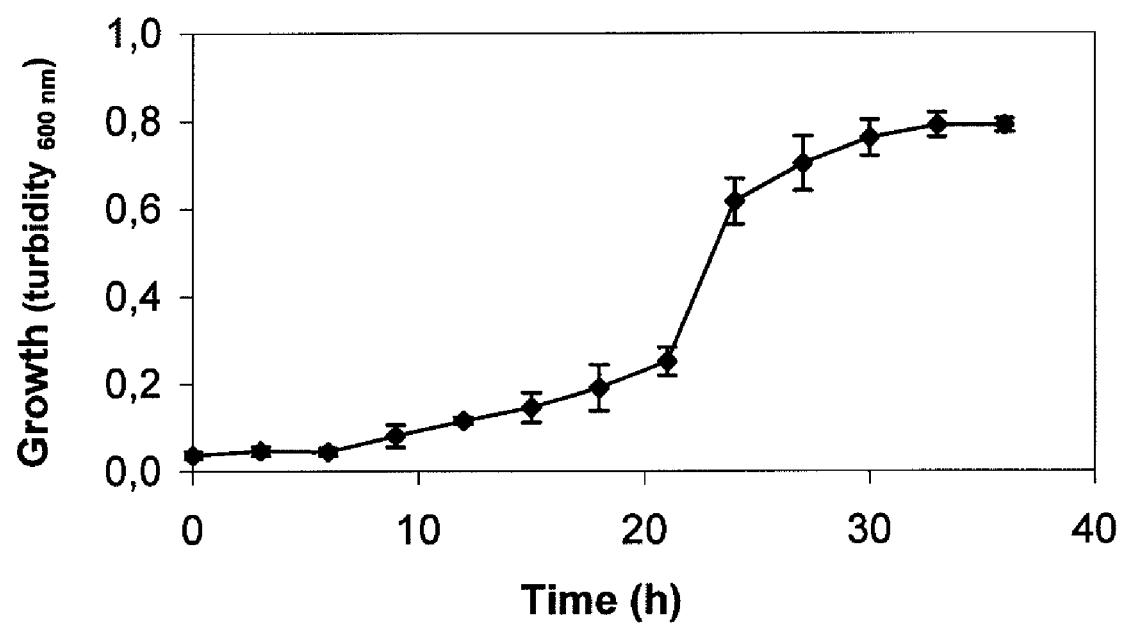
FIG. 3 shows the growth of *Pseudomonas* sp. strain MPH41 using simazine as the sole nitrogen source. The growth was followed measuring turbidity at 600 nm and the growth values are the mean of 3 independent experiments.

FIG. 3 shows the growth curve of Pseudomonas sp. Strain MPH41. Cells were grown in AM minimal medium using simazine as the sole nitrogen source and succinate as the sole carbon source. Growth was monitored by measuring turbidity at 600 nm with a Lambda 11 spectrophotometer (Perkin Elmer). Results were obtained for 3 independent experiments. Growth was observed for the native Pseudomonas sp. strain MHP41, reaching the exponential phase after 24 hours and reaching the stationary phase with a turbidity of 0.8 ($1.5 \times 10^5$ CFU/ml) after 36 hours (FIG. 3).

Figure 4:
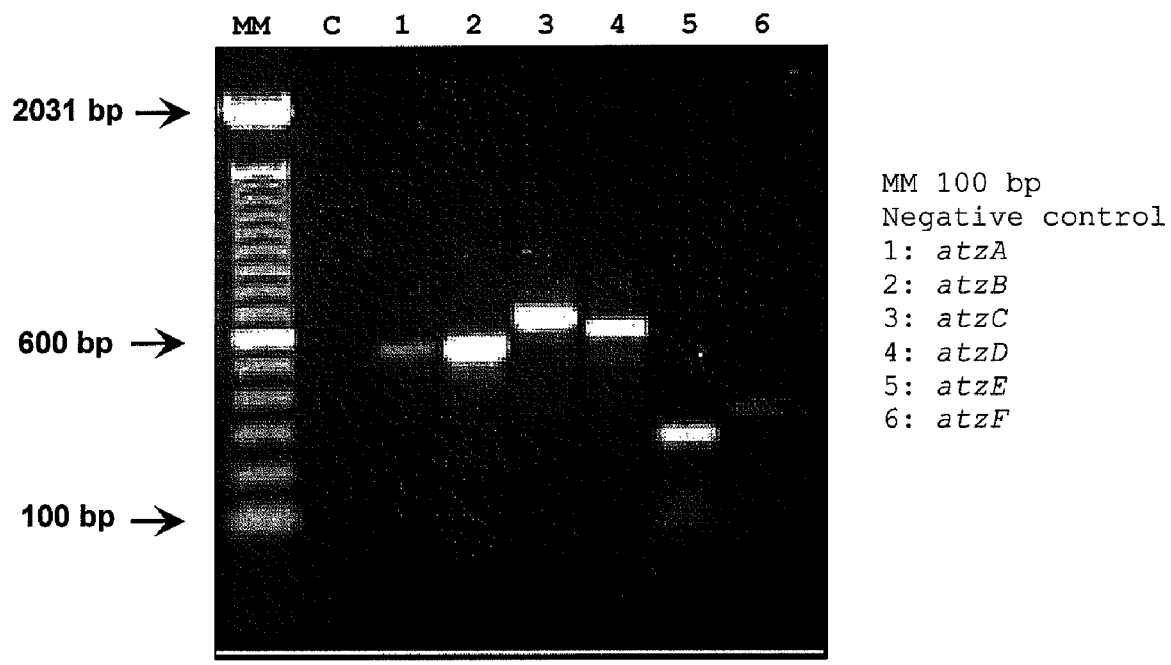
FIG. 4 shows the detection of atrazine catabolic atz genes in *Pseudomonas* sp. strain MHP41 by PCR using specific primers. PCR-amplification products: atzA (lane 1), atzB (lane 2), atzC (lane 3), atzD (lane 4), atzE (lane 5) and atzF (lane 6) of *Pseudomonas* sp. strain MHP41.

FIG. 4 shows the detection of the six degradation atz genes for s-triazines in Pseudomonas sp. strain MHP41. The amplification of the atz genes was carried out by PCR using specific primers previously described (de Souza et al., 1998). PCR products were analyzed by electrophoresis in agarose gel (1.2%) in TBE (0.5×) and were stained with ethidium bromide (FIG. 4).

It is important to mention that the isolated Pseudomonas sp. strain MHP41, is different to the strain described in the state of the art, Pseudomonas sp. strain ADP. Pseudomonas sp. strain MHP41 has important genetic and phenotypic differences with the reference strain Pseudomonas sp. ADP (Mandelbaum et al., 1996). Strain MHP41 has a different 16S rRNA gene sequence that strain ADP. This is the most used gene for bacterial taxonomy. Strain MHP41 can be genetically modified in the lab, incorporating plasmids of incompatibility series IncP, IncQ and Cryptic with high frequency. To date, there are no studies that describe the genetic modification of Pseudomonas sp. strain ADP.

Figure 5:
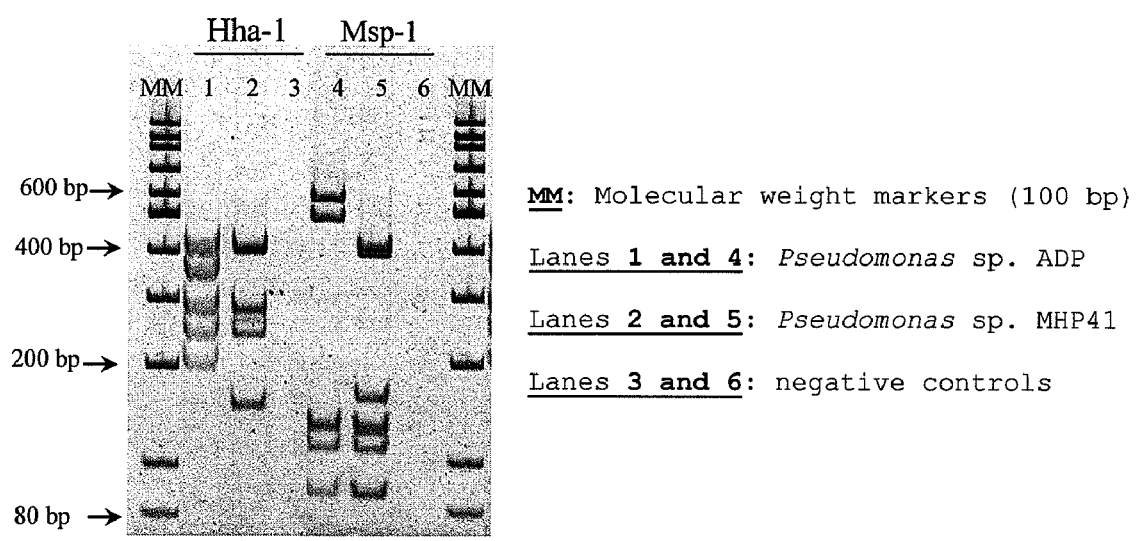
FIG. 5 shows the restriction profile of the ribosomal 16S rRNA gene of strains *Pseudomonas* sp. MHP41 and *Pseudomonas* sp. ADP. In this figure, lanes 2 and 5 correspond to *Pseudomonas* sp. MHP41, lanes 1 to 4 correspond to *Pseudomonas* sp. ADP and lanes 3 and 6 correspond to negative controls. 16S rRNA gene PCR-amplification products were digested with HhaI and MspI restriction enzymes. 100 pb molecular mass (MM) marker, is shown at the left side.

FIG. 5 shows the restriction profile of the 16S rRNA gene of the native strain *Pseudomonas* sp. MHP41 and the reference strain *Pseudomonas* sp. ADP. The Restriction Fragment Length Polymorphism (RFLP) analysis of the 16S rRNA genes were done by digestion with the restriction enzymes Msp-1 and Hha-1. Digestion with both enzymes generates differences in the restriction profiles of the 16S rRNA genes from both strains. Therefore, *Pseudomonas* sp. MHP41 and *Pseudomonas* sp. ADP are different ribotypes (FIG. 5).

In an additional embodiment, the present invention provide a product and a treatment method to improve the bioremediation of a contaminated environment with s-triazine herbicides such as simazine, hydroxysimazine, deethylhydroxysimazine, atrazine, hydroxyatrazine, deethylatrazine, deethylhydroxyatrazine, deisopropylatrazine, fluoroatrazine, propazine, terbutylazine, cyanuric acid and cyanazine.

In addition, the product provided by the present invention comprises an inoculum of the native *Pseudomonas* sp. strain MHP41 and a culture medium or a buffer solution or sodium alginate. This inoculum contains a known concentration of *Pseudomonas* sp. strain MHP41 (NRRL B-30908) ranging from $1 \times 10^3$ CFU/ml to $1 \times 10^{15}$ CFU/ml of culture medium or buffer solution, or from $1 \times 10^5$ CFU/g to $1 \times 10^{12}$ CFU/g of sodium alginate. Preferentially, the bacteria of the present invention have been previously grown in a minimal medium with simazine as the only nitrogen source.

In a preferred embodiment, the product provided by the present invention comprises an inoculum of *Pseudomonas* sp. strain MHP41 and the bacterial cells are encapsulated in a sodium alginate matrix. This immobilization protects bacterial cells from adverse environmental conditions, decreases their exposure to toxic compounds, and thus increases their stability and viability (Cassidy et al., 1996). This product for s-triazine bioremediation contains an inoculum of the bacteria *Pseudomonas* sp. strain MHP41 at a concentration which ranges from about $\times 10^5$ CFU/g to about $1 \times 10^{12}$ CFU/g of alginate.

In an additional embodiment of the present invention, the product contains an inoculum of the lyophilized cells of native bacteria *Pseudomonas* sp. strain MHP41, which further improves their transport and commercialization. To obtain this product for bioremediation, the bacteria have been preserved in a latent state by lyophilization of a concentrated bacterial suspension using protective sterile complex media such as bovine serum, powdered defatted milk or yeast extract, an amino acid such as monosodium glutamate, a fatty acid such as meso-inositol, and also a carbohydrate such as glucose, lactose, raffinose or mannitol. The lyophilized inoculum can be directly incubated in a liquid or solid growth medium, preferably at 28° C. during 48 h to recover active cells. After this activation process, the previously lyophilized *Pseudomonas* sp. MHP41 cells are able to degrade s-triazines. The product for bioremediation contains this lyophilized inoculum of the bacteria which after suspension in a suitable volume yields a concentration ranging from about $10^5$ CFU/ml to $10^{12}$ CFU/ml of medium.

The product of the present invention can also be formulated as a suspension of *Pseudomonas* sp. strain MHP41 in a liquid culture medium. Many culture media could be used for this purpose, and any of them could be used within the scope of the present invention, especially preferring minimal media described in Table 3, included in Example 2 of the present document. Said suspension comprises a known concentration of *Pseudomonas* sp. strain MHP41 NRRL B-30908 ranging from about $1 \times 10^3$ CFU/ml to $1 \times 10^{15}$ CFU/ml, preferably from $1 \times 10^5$ CFU/ml to $1 \times 10^{12}$ CFU/ml.

In a preferred embodiment of the invention, the bioremediation method comprises the addition of the product containing *Pseudomonas* sp. strain MHP41 to the environment contaminated with s-triazine compounds, such as simazine. In the method of the present invention, the bacteria are able to degrade completely the s-triazine compound, such as simazine. The product used for bioremediation can be applied as an inoculum of *Pseudomonas* sp. strain MHP41 encapsulated in a sodium alginate matrix, or an active suspension of the lyophilized product of *Pseudomonas* sp. strain MHP41 cells, or a suspension of *Pseudomonas* sp. strain MHP41 in a culture medium. After the inoculation into the contaminated environment of the product previously described in the embodiments of the present invention, the bacteria degrade the s-triazine compound of the contaminated environment during a period of time, from at least 1 week to about 12 months. Normally, a period from 1 to 4 weeks should be enough for an effective degradation of the contaminant. The concentration of *Pseudomonas* sp. strain MHP41 NRRL B-30908 in the contaminated environment which is usually soil, ranges from $1 \times 10^2$ CFU/g of soil to about $1 \times 10^{12}$ CFU/g of soil.

EXAMPLE 1

Isolation of *Pseudomonas* sp. Strain MHP41

The isolation of *Pseudomonas* sp. strain MHP41 was carried out by enrichment using simazine as the sole nitrogen source. For the isolation AM minimal medium (Table 3) was used, which has a saline fraction providing the micronutrients, succinate as the sole carbon source and saturated simazine as the sole nitrogen source. For the initial enrichment culture, samples were taken directly from agricultural soils. Cultures were incubated at 28° C. and then subcultures were grown. From these subcultures, bacteria were isolated in minimal agar plates using simazine as the sole nitrogen source. Individual colonies were isolated from the agar plates. These strains were conserved in glycerol (20%) at −24° C.

After this procedure, the native strain described in the present invention was obtained, i.e. *Pseudomonas* sp. MHP41. This bacterial strain has the capability to grow using simazine as the sole only nitrogen source. This strain was deposited in the microorganism collection Agricultural Research Culture Collection (NRRL) at Peoria, Ill., United States, under the accession number NRRL B-30908, on Mar. 17, 2006.

EXAMPLE 2

Maintenance and Conservation of the Product Containing *Pseudomonas* sp. MHP41

*Pseudomonas* sp. strain MHP41 is kept viable in the laboratory by culturing in different minimal media which composition is detailed in Table 3.

As alternative conservation methods, lyophilization processes and an encapsulation processes using sodium alginate was developed for the strain. For the lyophilization process, a protective sterile complex medium such as bovine serum, powdered defatted milk or yeast extract, an amino acid such as monosodium glutamate, a fatty acid such as meso-inositol, a carbohydrate such as glucose, lactose, raffinose or mannitol and also glycerol or dimethylsulfoxide are used.

In all the culture media and conservation methods, the viability and biodegrading capability of *Pseudomonas* sp. strain MHP41 is not reduced.

TABLE 3

Table 3. Minimal media formulations for maintenance of the native *Pseudomonas* sp. strain MHP41. To prepare solid media it is supplemented with 15 g/L agar.

| Name | Composition (g/L) | Carbon and Nitrogen Sources |
|---|---|---|
| AM | $K_2HPO_4$ 1.6 g; $KH_2PO_4$ 0.4 g; $MgSO_4 \times 7H_2O$ 0.2 g; NaCl 0.1 g; $CaCl_2$ 0.02 g; 20 ml of trace element solution containing (per liter): EDTA 2.5 g; $ZnSO_4$ 11.1 g; $FeSO_4$ 5 g; $MnSO_4 \times H_2O$ 1.54 g; $CuSO_4 \times 5H_2O$ 0.4 g; $Co(NO_3)_2 \times 6H_2O$ 0.25 g; $Na_2B_4O_7 \times 10H_2O$ 0.18 g and $H_2SO_4$ 5 ml. | Carbon Source: Sodium succinate 2.5 mM |
| Minimal medium (MM) | 100 ml phosphate buffer 10×, 2 ml of microelement solution 500×. Phosphate buffer 1× contains (per liter): 70 g $Na_2HPO_4 \times 2H_2O$, 28 g $KH_2PO_4$ and 5 g NaCl. Microelement solution 500× contains (per 100 ml): 5 g $MgSO_4 \times 7H_2O$, 0.5 g $FeSO_4 \times 7H_2O$, 0.25 g $MnSO_4 \times H_2O$, 0.32 g $ZnCl_2$, 0.033 g $CaCl_2 \times 2H_2O$, 0.018 g $CuSO_4 \times 5H_2O$, 0.015 g $CoCl_2 \times 6 H_2O$, 0.325 g $H_3BO_3$, 0.5 g EDTA, 7.3 ml HCl 37%. | Nitrogen Source: Simazine 0.5 mM For solid media 3 mM final concentration was used. |
| BSMA | $K_2HPO_4$ 0.5 g; $MgSO_4 \times 7H_2O$ 0.5 g; $FeCl_3 \times H_2O$ 10 mg; $CaCl_2 \times H_2O$ 10 mg; $MnCl_2$ 0.1 mg; $ZnSO_4$ 0.01 mg. | |
| Brunner | $Na_2HPO_4$ 2.44 g; $KH_2PO_4$ 1.52 g; $MgSO_4 \times 7H_2O$ 0.2 g; $CaCl_2 \times 2H_2O$ 0.05 g; 10 ml o fan element trace solution containing (per liter): EDTA 0.5 g; $FeSO_4 \times 7H_2O$ 0.2 g; 100 ml of an element trace solution containing (per liter): $ZnSO_4 \times 7H_2O$ 0.1 g; $MnCl_2 \times 4H_2O$ 0.03 g; $H_3BO_3$ 0.3 g; $CoCl_2 \times 6H_2O$ 0.2 g; $CuCl_2 \times 2H_2O$ 0.01 g; $NiCl_2 \times 6H_2O$ 0.02 g; $Na_2MoO_4 \times 2H_2O$ 0.03 g. | |

EXAMPLE 3

Degradation of the Simazine Compound by *Pseudomonas* sp. MHP41

Figure 6:
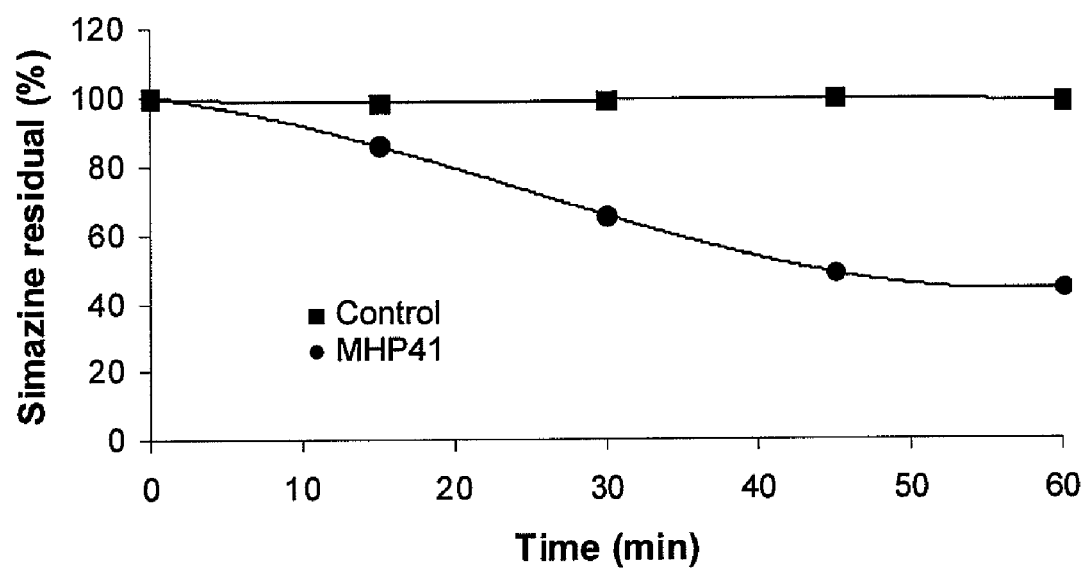
FIG. 6 shows the simazine-degradation kinetics by *Pseudomonas* sp. strain MHP41. The values indicate the mean of 3 independent experiments.

The ability of *Pseudomonas* sp. MHP41 to degrade simazine was assessed. Therefore, the bacterial strain MHP41 was cultured in AM medium using simazine as the sole nitrogen source at 30° C. for 16-20 h until the exponential phase (turbidity at 600 nm of 0.3; $7 \times 10^7$ CFU/ml). Cells were centrifuged and washed with sodium phosphate buffer [60 mM sodium phosphate (pH 7.0), 0.5 g NaCl liter$^{-1}$] and resuspended in U buffer [10 mM sodium phosphate (pH 7.0), 0.1 mM $MgSO_4$] into a turbidity at 600 nm of 2.5-3.0. The cultures were incubated at 30° C. with simazine at a final concentration of 0.06 mM. Culture medium without bacteria was used as a control. Samples were taken at 15 minutes intervals and these were centrifuged for 1 minute at 13,000 rpm. Simazine concentration was quantified by measuring absorbance at 225 nm using a spectrophotometer. The strain was able to degrade about 50% of the simazine compound after one hour of incubation. FIG. 6 shows a simazine degradation kinetic of *Pseudomonas* sp. strain MHP41. Results shown were obtained from 3 independent experiments (FIG. 6). In addition, the strain MHP41 grown in minimal medium using different nitrogen sources has the capability to degrade simazine Table 4).

TABLE 4

Table 4. Simazine degradation by *Pseudomonas* sp. MHP41 grown in minimal medium with different nitrogen sources.

| Growth (Nitrogen Sources) | Simazine degradation |
|---|---|
| Ammonium | + |
| Nitrate | + + |
| Urea | + + |
| Cyanuric acid | + + + |
| Simazine | + + + + |
| Atrazine | + + + + |

EXAMPLE 4

Figure 7:
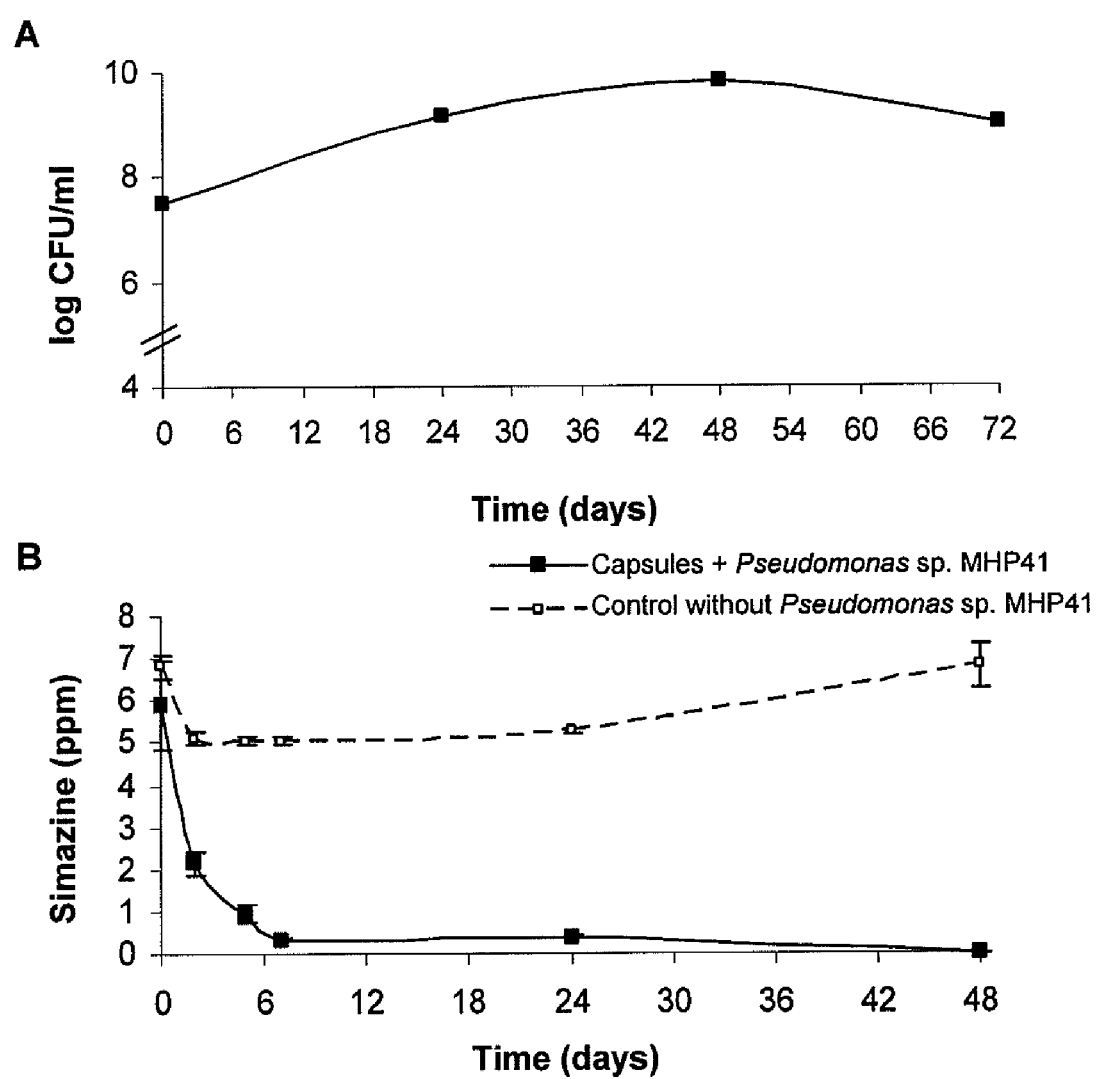
FIG. 7 shows the growth and simazine degradation by immobilized *Pseudomonas* sp. MHP41 in sodium alginate. A. Growth (turbidity at 600 nm) of strain MHP41 immobilized in sodium alginate matrix. B. Simazine degradation in aqueous medium. Microcapsules were incubated in AM minimal medium with simazine as the sole nitrogen source. Each value is the mean of three independent experiments.

Viability and Simazine Degrading Ability of *Pseudomonas* sp. MHP41 in Sodium Alginate Matrix A culture of *Pseudomonas* sp. MHP41 containing $1 \times 10^8$ CFU/ml (turbidity at 600 nm of 0.5) was encapsulated in 1% sodium alginate. The beads were stabilized in calcium chloride (9.3 g l$^{-1}$), kept in $CaCl_2$ and refrigerated at 4° C. Viability of encapsulated strain MHP41 was carried out according to the following procedure. 1 g of microcapsules was inoculated in minimal medium AM 0.4× with simazine 0.5 mM. Under this condition, the sodium alginate matrix is able to maintain its texture and integrity. Serial dilutions were carried out in 0.85% NaCl and were then plated in Trypticase Soy Agar (TSA) medium. TSA plates were incubated at 30° C. and *Pseudomonas* sp. MHP41 colonies were counted in the agar plates. Simazine was quantified by HPLC. At the beginning of the experiment, $1.2 \times 10^7$ CFU/ml was detected from the alginate beads. The number of viable cells increases during incubation time, reaching $3\times10^9$ CFU/ml after 72 hours. The encapsulation process with 1% sodium alginate allows the growth of *Pseudomonas* sp. MHP41, and do not affect its viability (FIG. 7). For simazine quantification by HPLC, simazine was extracted from the culture media samples with methanol/water (80:20). The simazine degradation capability of *Pseudomonas* sp. MHP41 was not reduced by encapsulation in sodium alginate matrix. The simazine (0.5 mM) was removed from the liquid AM medium in less than 48 hours. Sodium alginate capsules without bacteria do not remove simazine from the medium. Results were obtained from 3 independent experiments (FIG. 7).

EXAMPLE 5

Bioremediation with *Pseudomonas* sp. Strain MHP41 of Simazine in Soil

The bioremediation experiments at the microcosms scale were performed to study simazine degradation in agricultural soil by the addition of the native s-triazine-degrading *Pseudomonas* sp. strain MHP41.

The strain was analyzed in two different types of soil: i) soil without history of simazine application and ii) soil annually treated with simazine. Soil was collected from the surface layer (0 to 15 cm), sieved through 5-mm, 2.8-mm and 2-mm mesh sieves and then contaminated with commercial simazine (Gesatop® 90WP). *Pseudomonas* sp. strain MHP41 was grown in minimal medium containing simazine as the sole nitrogen source and was added to the soil as immobilized inocula in sodium alginate matrix at a concentration of $1\times10^8$ CFU/g of dry soil (equivalent to a cell biomass of $1\times10^{12}$ CFU/ml). Microcosms were inoculated each 4 days during four weeks. Soil moisture was controlled weekly. Soil samples were collected for microbiological and analytical determinations in triplicate. Soil samples were used to estimate the total heterotrophic bacteria count (THC) in trypticase soy agar plates (TSA, OXOID). The Most Probably Number (MPN) method was performed to estimate the simazine catabolic activity in the soil. Simazine was quantified by HPLC following extraction from soil with methanol/water (80:20) solution.

Figure 8:
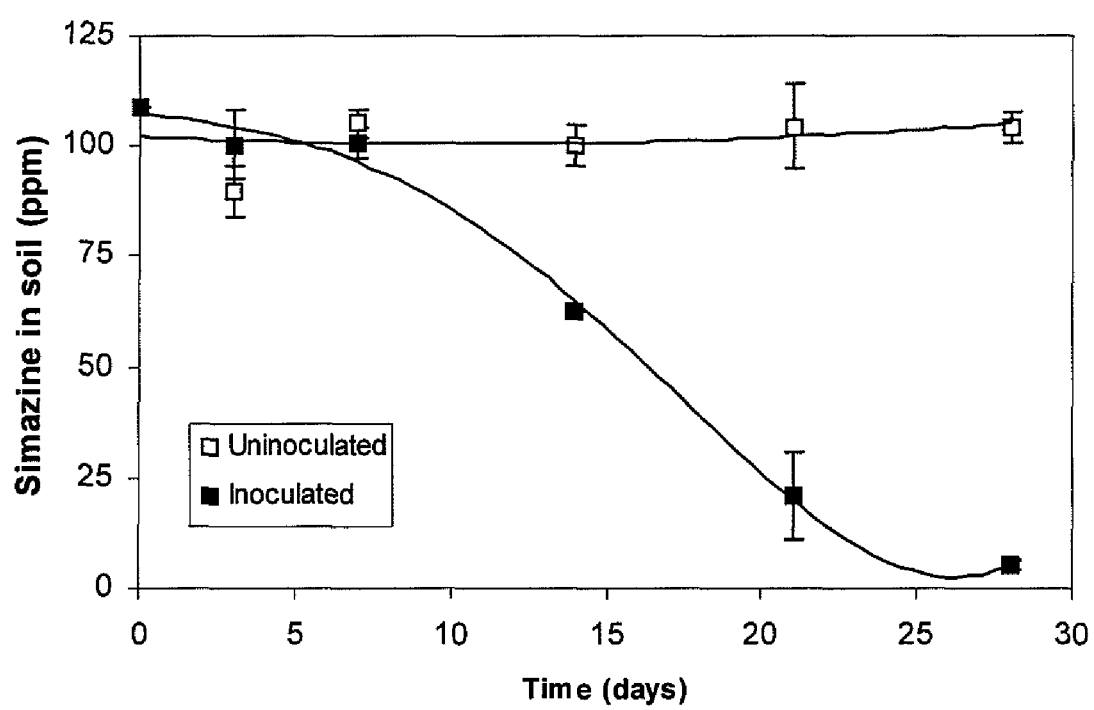
FIG. 8 shows simazine degradation kinetics by *Pseudomonas* sp. strain MHP41 during bioremediation in soil microcosms without history of simazine application. During bioaugmentation with encapsulated *Pseudomonas* sp. strain MHP41, 50% of the herbicide is degraded after 15 days. Herbicide attenuation is not observed in control soil after 28 days.

In soil previously not exposed to simazine, i.e. soil with no history of simazine application (FIG. 8), bioaugmentation with *Pseudomonas* sp. MHP41 increased the total heterotrophic bacteria count and simazine catabolic activities. In none inoculated treatments, no active simazine-degrading microbial population was detected and no herbicide removal was observed. Bioaugmentation with *Pseudomonas* sp. strain MHP41 increased the simazine catabolic activity and attenuated the simazine concentration in the soil with a half-life of 15 days (FIG. 8).

Figure 9:
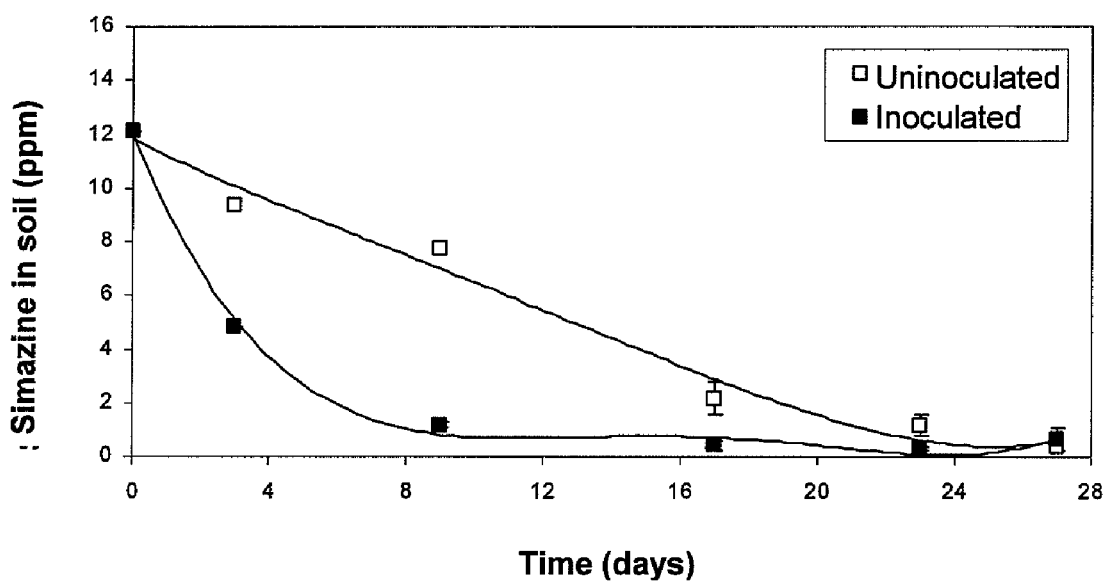
FIG. 9 shows simazine degradation kinetic by *Pseudomonas* sp. strain MHP41 during bioremediation in soil microcosms with history of simazine application. Three days after *Pseudomonas* sp. strain MHP41 application, 50% of the applied simazine was attenuated. By bioaugmentation, 90% of the applied simazine is removed in soil after 15 days. In non-inoculated soil, simazine removal takes at least 25 days.

In soils with history of simazine herbicide application (FIG. 9), the total heterotrophic bacteria count showed minimal changes between inoculated and none inoculated treatments. Furthermore, the simazine half-life in uninoculated microcosms was 11 days. When soils were bioaugmented, the simazine half-life was reduced to 3 days. Complete simazine attenuation in the inoculated treatment was observed after 24 days (FIG. 9).

This example demonstrates that the native *Pseudomonas* sp. strain MHP41 increases the catabolic activity in both types of soil with different simazine application histories. Furthermore, the addition of this encapsulated strain attenuates the concentration of herbicide in both type of soils. Therefore it can be used for bioremediation strategies.

EXAMPLE 6

Bioremediation of Simazine in Soil with Lyophilized *Pseudomonas* sp. Strain MHP41

To evaluate the simazine-degrading potential of *Pseudomonas* sp. strain MHP41 in agricultural soil, bioremediation experiments in microcosms were performed using lyophilized cells of the strain. Lyophilized cells of strain MHP41 were activated in liquid AM minimal medium and added to the soil following the same experimental set-up described in Example 5. Simazine attenuation was observed, and a decrease of about 50% of simazine was obtained in the soil during the first week of incubation.

This example, demonstrates that the lyophilized process does not affect the simazine-degrading ability of *Pseudomonas* sp. strain MHP41 in the soil.

References

Cassidy, M. B., H. Lee, and J. T. Trevors. 1996. Environmental applications of immobilized microbial cells: a review. J Ind Microbiol Biotechnol 16:79-101.

Cheng, G., Shapir, N., Sadowsky, M. J., and L. Wackett. 2005. Allophanate Hydrolase, not Urease, functions in bacterial cyanuric acid metabolism. Appl. Environ. Microbiol. 71:4437-4445.

de Souza, M. L., J. Seffernick, B. Martinez, M. Sadowsky, and L. P. Wackett. 1998. The atrazine catabolism genes atzABC are widespread and highly conserved. J. Bacteriol. 180:1951-1954.

Mandelbaum, R. T. and L. P. Wackett. 1996. *Pseudomonas* strain for degradation of s-triazines in soil and water. U.S. Pat. No. 5,508,193. USA.

Rousseaux, S., A. Hartmann, and G. Soulas. 2001. Isolation and characterisation of new Gram-negative and Gram-positive atrazine degrading bacteria from different French soils. FEMS Microbiol. Ecol. 36:211-222.

Tappe, W., J. Groeneweg and B. Jantsch. 2002. Diffuse atrazine pollution in German aquifers. Biodegradation 13:3-10.

The invention claimed is:

1. A biologically pure culture of *Pseudomonas* sp. strain NRRL B-30908 which is able to degrade or mineralize s-triazine compounds.

2. A product for the bioremediation of s-triazine-contaminated environments, including a bacterial inoculum of a biologically pure culture of *Pseudomonas* sp. strain NRRL B-30908, according to claim 1, and a culture medium, a buffer solution or sodium alginate.

3. The product for the bioremediation according to claim 2, wherein the inoculum contains said biologically pure culture of *Pseudomonas* sp. strain NRRL B-30908 in an amount of from $1\times10^3$ colony forming units (CFU)/ml to about $1\times10^{15}$ CFU/ml of said culture medium or said buffer solution or in an amount of from $1\times10^5$ CFU/g to about $1\times10^{12}$ CFU/g of said sodium alginate.

4. A method for the bioremediation of a s-triazine-contaminated environment, comprising the steps of:
   a) adding the product according to claim 2, to the environment contaminated with s-triazine compounds, and
   b) incubating the product, in the environment for a period of time sufficient to permit the complete degradation of the s-triazine compounds in the environment, wherein the period of time ranges from at least 1 week to about 12 months.

5. The method for the bioremediation of a s-triazine-contaminated environment according to claim 4, wherein the period of time ranges from 1 week to 4 weeks.

6. The method for the bioremediation of a s-triazine-contaminated environment according to claim 4, wherein the concentration of a biologically pure culture of *Pseudomonas* sp. strain NRRL B-30908 ranges from about $1\times10^2$ CFU/g of soil to about $1\times10^{12}$ CFU/g of soil in the contaminated environment.

7. The method for the bioremediation of a s-triazine-contaminated environment according to claim 4, wherein the s-triazine compounds in the contaminated environment are selected from the group consisting of simazine, hydroxysimazine, deethylhydroxysimazine, atrazine, hydroxyatrazine, deethylatrazine, deethylhydroxyatrazine, deisopropylatrazine, fluoroatrazine, propazine, terbutylazine, cyanuric acid and cyanazine.

8. The method for the bioremediation of a s-triazine-contaminated environment according to claim 4, wherein the s-triazine compounds contain a chlorine atom.

9. The method for the bioremediation of a s-triazine-contaminated environment according to claim 8, wherein said s-triazine compounds include simazine.

10. The method for the bioremediation of a s-triazine-contaminated environment according to claim 8, wherein said s-triazine compounds include atrazine.

11. A product for the bioremediation of s-triazine-contaminated environments, including lyophilized cells of a biologically pure culture of *Pseudomonas* sp. strain NRRL B-30908 in a sterile complex protective medium.

12. A product for the bioremediation of s-triazine-contaminated environments, including immobilized cells of a biologically pure culture of *Pseudomonas* sp. strain NRRL B-30908 in sodium alginate.

* * * * *

UNITED STATES PATENT AND TRADEMARK OFFICE
CERTIFICATE OF CORRECTION

PATENT NO. : 8,263,385 B2  
APPLICATION NO. : 12/166961  
DATED : September 11, 2012  
INVENTOR(S) : Hernandez et al.

Page 1 of 1

It is certified that error appears in the above-identified patent and that said Letters Patent is hereby corrected as shown below:

On the Title page, [73]: "Universidad Technica Fedrico Santa Maria, Valparaiso (CL)" should read --Universidad Tecnica Federico Santa Maria, Valparaiso (CL)--

Signed and Sealed this  
Twenty-fifth Day of March, 2014

Michelle K. Lee  
*Deputy Director of the United States Patent and Trademark Office*